(12) United States Patent
Thapliyal et al.

(10) Patent No.: US 11,207,549 B2
(45) Date of Patent: *Dec. 28, 2021

(54) SYSTEM AND METHOD FOR DELIVERING ENERGY TO TISSUE

(71) Applicant: Auris Health, Inc., Redwood City, CA (US)

(72) Inventors: Hira V. Thapliyal, Los Altos, CA (US); David A. Gallup, Alameda, CA (US); James W. Arenson, Woodside, CA (US)

(73) Assignee: Auris Health, Inc., Redwood City, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/439,805

(22) Filed: Jun. 13, 2019

(65) Prior Publication Data

US 2020/0155192 A1 May 21, 2020

Related U.S. Application Data

(63) Continuation of application No. 13/630,674, filed on Sep. 28, 2012, now Pat. No. 10,368,891, which is a
(Continued)

(51) Int. Cl.
*A61N 7/02* (2006.01)
*A61B 17/22* (2006.01)
(Continued)

(52) U.S. Cl.
CPC .......... *A61N 7/022* (2013.01); *A61B 17/2202* (2013.01); *A61B 17/320068* (2013.01);
(Continued)

(58) Field of Classification Search
CPC .... A61N 2007/0043; A61N 2007/0069; A61N 2007/006; A61N 7/00; A61N 7/02; A61N 7/2202; A61B 8/00; A61B 8/12
See application file for complete search history.

(56) References Cited

U.S. PATENT DOCUMENTS

| 4,641,649 | A | 2/1987 | Walinsky et al. |
| 4,708,127 | A | 11/1987 | Abdelghani |

(Continued)

FOREIGN PATENT DOCUMENTS

| DE | 10037660 A1 | 2/2002 |
| EP | 2540348 A1 | 1/2013 |

(Continued)

OTHER PUBLICATIONS

A new treatment for atrial fibrillation? Feb. 2006, Medical Device & Diagnostic Industry, Medical Device Link, http://www.devicelink.com/mddi/archive/06/02/013.html (2 pgs.).
(Continued)

*Primary Examiner* — Carolyn A Pehlke
(74) *Attorney, Agent, or Firm* — Chang & Hale LLP

(57) ABSTRACT

An ablation system for treating atrial fibrillation in a patient comprises an elongate shaft having proximal and distal ends, a lumen therebetween and a housing adjacent the distal end of the elongate shaft. An energy source is coupled to the housing and is adapted to deliver energy to a target tissue so as to create a zone of ablation in the target tissue that blocks abnormal electrical activity thereby reducing or eliminating the atrial fibrillation in the patient. A sensor is adjacent the energy source and adapted to detect relative position of the energy source to the target tissue or characteristics of the target tissue. The system also has a reflecting element operably coupled with the energy source and adapted to redirect energy emitted from the energy source in a desired direction or pattern.

20 Claims, 6 Drawing Sheets

Related U.S. Application Data continuation of application No. 12/505,335, filed on Jul. 17, 2009.

(60) Provisional application No. 61/082,064, filed on Jul. 18, 2008.

(51) Int. Cl.
*A61B 17/32* (2006.01)
*A61B 17/00* (2006.01)
*A61N 7/00* (2006.01)
*A61B 18/14* (2006.01)
*A61B 18/18* (2006.01)
*A61B 18/00* (2006.01)
*A61B 18/02* (2006.01)

(52) U.S. Cl.
CPC ............ *A61B 18/148* (2013.01); *A61B 18/18* (2013.01); *A61B 2017/00106* (2013.01); *A61B 2017/22051* (2013.01); *A61B 2017/320069* (2017.08); *A61B 2018/00011* (2013.01); *A61B 2018/00023* (2013.01); *A61B 2018/00577* (2013.01); *A61B 2018/0262* (2013.01); *A61B 2018/1807* (2013.01); *A61N 2007/0052* (2013.01); *A61N 2007/0091* (2013.01)

(56) References Cited

U.S. PATENT DOCUMENTS

| | | |
|---|---|---|
| 4,757,820 A | 7/1988 | Itoh |
| 4,858,613 A | 8/1989 | Fry et al. |
| 5,010,886 A | 4/1991 | Passafaro et al. |
| 5,024,234 A | 6/1991 | Leary et al. |
| 5,029,588 A | 7/1991 | Yock et al. |
| 5,246,438 A | 9/1993 | Langberg |
| 5,295,484 A | 3/1994 | Marcus et al. |
| 5,314,466 A | 5/1994 | Stern et al. |
| 5,405,346 A | 4/1995 | Grundy et al. |
| 5,647,367 A | 7/1997 | Lum et al. |
| 5,718,241 A | 2/1998 | Ben-Haim et al. |
| 5,735,811 A | 4/1998 | Brisken |
| 6,012,457 A | 1/2000 | Lesh |
| 6,024,740 A | 2/2000 | Lesh et al. |
| 6,050,943 A | 4/2000 | Slayton et al. |
| 6,052,576 A | 4/2000 | Lambourg |
| 6,064,902 A | 5/2000 | Haissaguerre et al. |
| 6,117,101 A | 9/2000 | Diederich et al. |
| 6,161,543 A | 12/2000 | Cox et al. |
| 6,164,283 A | 12/2000 | Lesh |
| 6,237,605 B1 | 5/2001 | Vaska et al. |
| 6,245,064 B1 | 6/2001 | Lesh et al. |
| 6,245,095 B1 | 6/2001 | Dobak, III et al. |
| 6,251,129 B1 | 6/2001 | Dobak, III et al. |
| 6,251,130 B1 | 6/2001 | Dobak, III et al. |
| 6,254,599 B1 | 7/2001 | Lesh et al. |
| 6,261,312 B1 | 7/2001 | Dobak, III et al. |
| 6,277,116 B1 | 8/2001 | Utely et al. |
| 6,305,378 B1 | 10/2001 | Lesh |
| 6,311,090 B1 | 10/2001 | Knowlton |
| 6,311,692 B1 | 11/2001 | Vaska et al. |
| 6,314,962 B1 | 11/2001 | Vaska et al. |
| 6,314,963 B1 | 11/2001 | Vaska et al. |
| 6,315,732 B1 | 11/2001 | Suorsa et al. |
| 6,379,378 B1 | 4/2002 | Werneth et al. |
| 6,383,151 B1 | 5/2002 | Diederich et al. |
| 6,387,089 B1 | 5/2002 | Kreindel et al. |
| 6,416,511 B1 | 7/2002 | Lesh et al. |
| 6,468,296 B1 | 10/2002 | Dobak, III et al. |
| 6,474,340 B1 | 11/2002 | Vaska et al. |
| 6,475,231 B2 | 11/2002 | Dobak et al. |
| 6,478,811 B1 | 11/2002 | Dobak, III et al. |
| 6,478,812 B2 | 11/2002 | Dobak et al. |
| 6,484,727 B1 | 11/2002 | Vaska et al. |
| 6,491,039 B1 | 12/2002 | Dobak, III |
| 6,491,716 B2 | 12/2002 | Dobak et al. |
| 6,500,121 B1 | 12/2002 | Slayton et al. |
| 6,500,174 B1 | 12/2002 | Maguire et al. |
| 6,502,576 B1 | 1/2003 | Lesh |
| 6,514,244 B2 | 2/2003 | Pope et al. |
| 6,514,249 B1 | 2/2003 | Maguire et al. |
| 6,517,536 B2 | 2/2003 | Hooven et al. |
| 6,529,756 B1 | 3/2003 | Phan et al. |
| 6,533,804 B2 | 3/2003 | Dobak et al. |
| 6,540,771 B2 | 4/2003 | Dobak et al. |
| 6,542,781 B1 | 4/2003 | Koblish et al. |
| 6,546,935 B2 | 4/2003 | Hooven |
| 6,547,788 B1 | 4/2003 | Maguire et al. |
| 6,551,349 B2 | 4/2003 | Lasheras et al. |
| 6,576,001 B2 | 6/2003 | Werneth et al. |
| 6,585,752 B2 | 7/2003 | Dobak et al. |
| 6,592,576 B2 | 7/2003 | Andrews et al. |
| 6,595,989 B1 | 7/2003 | Schaer |
| 6,599,288 B2 | 7/2003 | Maguire et al. |
| 6,602,276 B2 | 8/2003 | Dobak, III et al. |
| 6,605,084 B2 | 8/2003 | Acker et al. |
| 6,607,502 B1 | 8/2003 | Maguire et al. |
| 6,607,527 B1 | 8/2003 | Ruiz et al. |
| 6,613,046 B1 | 9/2003 | Jenkins et al. |
| 6,635,054 B2 | 10/2003 | Fjield et al. |
| 6,645,144 B1 | 11/2003 | Wen et al. |
| 6,645,199 B1 | 11/2003 | Jenkins et al. |
| 6,645,202 B1 | 11/2003 | Pless et al. |
| 6,648,908 B2 | 11/2003 | Dobak et al. |
| 6,652,515 B1 | 11/2003 | Maguire et al. |
| 6,652,517 B1 | 11/2003 | Hall et al. |
| 6,666,614 B2 | 12/2003 | Fechter et al. |
| 6,666,858 B2 | 12/2003 | Lafontaine |
| 6,669,655 B1 | 12/2003 | Acker et al. |
| 6,669,687 B1 | 12/2003 | Saadat |
| 6,676,688 B2 | 1/2004 | Dobak et al. |
| 6,676,689 B2 | 1/2004 | Dobak et al. |
| 6,676,690 B2 | 1/2004 | Werneth |
| 6,685,732 B2 | 2/2004 | Kramer |
| 6,689,128 B2 | 2/2004 | Sliwa et al. |
| 6,692,488 B2 | 2/2004 | Dobak et al. |
| 6,695,873 B2 | 2/2004 | Dobak et al. |
| 6,701,931 B2 | 3/2004 | Sliwa et al. |
| 6,702,842 B2 | 3/2004 | Dobak et al. |
| 6,711,444 B2 | 3/2004 | Koblish |
| 6,719,755 B2 | 4/2004 | Sliwa et al. |
| 6,745,080 B2 | 6/2004 | Koblish |
| 6,752,805 B2 | 6/2004 | Maguire et al. |
| 6,758,847 B2 | 7/2004 | Maguire |
| 6,763,722 B2 | 7/2004 | Fjield et al. |
| 6,780,183 B2 | 8/2004 | Jimenez et al. |
| 6,786,218 B2 | 9/2004 | Dobak et al. |
| 6,805,128 B1 | 10/2004 | Pless et al. |
| 6,805,129 B1 | 10/2004 | Pless et al. |
| 6,814,733 B2 | 11/2004 | Schwartz et al. |
| 6,840,936 B2 | 1/2005 | Sliwa et al. |
| 6,858,026 B2 | 2/2005 | Sliwa et al. |
| 6,869,431 B2 | 3/2005 | Maguire et al. |
| 6,872,205 B2 | 3/2005 | Lesh et al. |
| 6,889,694 B2 | 5/2005 | Hooven |
| 6,893,438 B2 | 5/2005 | Hall et al. |
| 6,896,673 B2 | 5/2005 | Hooven |
| 6,899,710 B2 | 5/2005 | Hooven |
| 6,899,711 B2 | 5/2005 | Stewart et al. |
| 6,904,303 B2 | 6/2005 | Phan et al. |
| 6,905,494 B2 | 6/2005 | Yon et al. |
| 6,905,498 B2 | 6/2005 | Hooven |
| 6,905,509 B2 | 6/2005 | Dobak et al. |
| 6,908,464 B2 | 6/2005 | Jenkins et al. |
| 6,920,883 B2 | 7/2005 | Bessette et al. |
| 6,923,806 B2 | 8/2005 | Hooven et al. |
| 6,923,808 B2 | 8/2005 | Taimisto |
| 6,929,639 B2 | 8/2005 | Lafontaine |
| 6,932,811 B2 | 8/2005 | Hooven et al. |
| 6,949,095 B2 | 9/2005 | Vaska et al. |
| 6,949,097 B2 | 9/2005 | Stewart et al. |
| 6,953,460 B2 | 10/2005 | Maguire et al. |
| 6,954,977 B2 | 10/2005 | Maguire et al. |
| 6,955,173 B2 | 10/2005 | Lesh |

(56) References Cited

U.S. PATENT DOCUMENTS

| | | |
|---|---|---|
| 6,964,660 B2 | 11/2005 | Maguire et al. |
| 6,966,908 B2 | 11/2005 | Maguire et al. |
| 6,971,394 B2 | 12/2005 | Sliwa et al. |
| 6,974,454 B2 | 12/2005 | Hooven |
| 6,984,233 B2 | 1/2006 | Hooven |
| 6,997,925 B2 | 2/2006 | Maguire et al. |
| 7,001,378 B2 | 2/2006 | Yon et al. |
| 7,001,415 B2 | 2/2006 | Hooven |
| 7,044,135 B2 | 5/2006 | Lesh |
| 7,063,682 B1 | 6/2006 | Whayne et al. |
| 7,142,905 B2 | 11/2006 | Slayton et al. |
| 7,275,450 B2 | 10/2007 | Hirai et al. |
| 7,285,116 B2 | 10/2007 | Rama et al. |
| 7,306,593 B2 | 12/2007 | Keidar et al. |
| 7,393,325 B2 | 7/2008 | Barthe et al. |
| 9,033,885 B2 | 5/2015 | Thapliyal et al. |
| 9,220,924 B2 | 12/2015 | Thapliyal et al. |
| 10,368,891 B2 | 8/2019 | Thapliyal et al. |
| 2001/0025185 A1 | 9/2001 | Laufer et al. |
| 2002/0045895 A1 | 4/2002 | Sliwa et al. |
| 2002/0065512 A1 | 5/2002 | Fjield et al. |
| 2002/0087151 A1 | 7/2002 | Mody et al. |
| 2002/0128636 A1 | 9/2002 | Chin et al. |
| 2003/0036729 A1 | 2/2003 | Jang |
| 2003/0050630 A1 | 3/2003 | Mody et al. |
| 2003/0050631 A1 | 3/2003 | Mody et al. |
| 2003/0060815 A1 | 3/2003 | Lalonde et al. |
| 2003/0125726 A1 | 7/2003 | Maguire et al. |
| 2003/0153907 A1 | 8/2003 | Suorsa et al. |
| 2003/0163128 A1 | 8/2003 | Patil et al. |
| 2003/0176816 A1 | 9/2003 | Maguire et al. |
| 2004/0015106 A1 | 1/2004 | Coleman |
| 2004/0082948 A1 | 4/2004 | Stewart et al. |
| 2004/0176757 A1 | 9/2004 | Sinelnikov et al. |
| 2005/0043726 A1 | 2/2005 | McHale et al. |
| 2005/0049582 A1 | 3/2005 | Debenedictis et al. |
| 2005/0070961 A1 | 3/2005 | Maki et al. |
| 2005/0131468 A1 | 6/2005 | Echt et al. |
| 2005/0165388 A1 | 7/2005 | Bhola |
| 2005/0256518 A1 | 11/2005 | Rama et al. |
| 2006/0058707 A1 | 3/2006 | Barthe et al. |
| 2006/0122508 A1 | 6/2006 | Slayton et al. |
| 2006/0155269 A1 | 7/2006 | Warnking |
| 2006/0287650 A1 | 12/2006 | Cao et al. |
| 2007/0015998 A1 | 1/2007 | Yock |
| 2007/0016072 A1 | 1/2007 | Grunwald et al. |
| 2007/0027445 A1 | 2/2007 | Gifford et al. |
| 2007/0083168 A1 | 4/2007 | Whiting et al. |
| 2007/0265609 A1 | 11/2007 | Thapliyal et al. |
| 2007/0265610 A1 | 11/2007 | Thapliyal et al. |
| 2007/0299496 A1 | 12/2007 | Podmore et al. |
| 2008/0039746 A1 | 2/2008 | Hissong et al. |
| 2008/0077200 A1 | 3/2008 | Bendett et al. |
| 2008/0161785 A1 | 7/2008 | Crowe et al. |
| 2009/0312673 A1 | 12/2009 | Thapliyal et al. |
| 2009/0312693 A1 | 12/2009 | Thapliyal et al. |
| 2010/0016762 A1 | 1/2010 | Thapliyal et al. |
| 2010/0152582 A1 | 6/2010 | Thapliyal et al. |

FOREIGN PATENT DOCUMENTS

| | | |
|---|---|---|
| EP | 2307098 B1 | 3/2015 |
| JP | 2005137916 A | 6/2005 |
| JP | 2007152094 A | 6/2007 |
| WO | WO-9902096 A1 | 1/1999 |
| WO | WO-03053259 A2 | 7/2003 |
| WO | WO-2004110258 A2 | 12/2004 |
| WO | WO-2004110258 A3 | 8/2005 |
| WO | WO-2005102199 A1 | 11/2005 |
| WO | WO-2005117734 A2 | 12/2005 |
| WO | WO-2006044662 A2 | 4/2006 |
| WO | WO-2006044662 A3 | 7/2006 |
| WO | WO-2005117734 A3 | 12/2006 |
| WO | WO-2010009472 A1 | 1/2010 |
| WO | WO-2010120883 A2 | 10/2010 |
| WO | WO-2010120883 A3 | 3/2011 |

OTHER PUBLICATIONS

Bushberg, et al. The essential physics of medical imaging. 2nd Ed.; Lippincott Williams & Wilkins; 2002; p. 491.
Cox, et al. Current status of the Maze procedure for the treatment of atrial fibrillation. Seminars in Thoracic & Cardiovascular Surgery. 2000; 12:15-19.
Cox, et al. Electrophysiologic basis, surgical development, and clinical results of the maze procedure for atrial flutter and atrial fibrillation. Advances in Cardiac Surgery. 1995; 6:1-67.
Cox, et al. Modification of the maze procedure for atrial flutter and atrial fibrillation. II, Surgical technique of the maze III procedure. Journal of Thoracic & Cardiovascular Surgery. 1995;110:485-95.
Cox, et al. The development of the Maze procedure for the treatment of atrial fibrillation. Seminars in Thoracic & Cardiovascular Surgery. 2000; 12:2-14.
Ehrenstein, D. New technique maps the body electric. Science 276. No. 5313 (1997): 681-681.
European search report and opinion dated Sep. 17, 2012 for EP Application No. 09798856.2.
European search report dated Oct. 30, 2012 for EP Application No. 12186735.2.
Gentry, et al. Integrated Catheter for 3-D Intracardiac Echocardiography and Ultrasound Ablation. IEEE Transactions on Ultrasonics, Ferroelectrics, and Frequency Control. 2004;51(7):800-808.
Gill. How to perform pulmonary vein isolation. Europace. 2004; 6(2):83-91.
Gillinov, et al. Atrial fibrillation: current surgical options and their assessment. Annals of Thoracic Surgery. 2002;74:2210-7.
Haissaguerre, et al. Spontaneous Initiation of Atrial Fibrillation by Ectopic Beats Originating in the Pulmonary Veins. New England J Med. 1998; 339:659-666.
International search report and written opinion dated Nov. 17, 2009 for PCT/US2009/051166.
Levinson. Endocardial Microwave Ablation: A New Surgical Approach for Atrial Fibrillation. The Heart urgery Forum. 2006 (5 pgs).
Maessen, et al. Beating heart surgical treatment of atrial fibrillation with microwave ablation. Ann Thorac Surg. 2002; 74: 1160-8.
Mosby's Medical Dictionary. Definition of term "duty cycle". 8th Edition. 2009. Retrieved Mar. 16, 2017. URL:< http://medical-dictionary.thefreedictionary.com/duty+cycle>.
Nathan, et al. The junction between the left atrium and the pulmonary veins, an anatomic study of human hearts. Circulation. 1966; 34:412-422.
"Office action dated Jan. 25, 2018 for U.S. Appl. No. 13/630,674.".
Office action dated Feb. 22, 2013 for U.S. Appl. No. 12/505,335.
Office action dated Feb. 28, 2014 for U.S. Appl. No. 13/630,674.
Office action dated Mar. 18, 2014 for U.S. Appl. No. 12/505,335.
Office Action dated Mar. 23, 2017 for U.S. Appl. No. 12/505,335.
Office action dated May 11, 2011 for U.S. Appl. No. 12/505,335.
Office action dated Jun. 6, 2016 for U.S. Appl. No. 13/630,674.
Office action dated Jun. 26, 2017 for U.S. Appl. No. 13/630,674.
"Office action dated Jul. 23, 2015 for U.S. Appl. No. 12/505,335.".
"Office action dated Jul. 23, 2015 for U.S. Appl. No. 13/630,674.".
Office action dated Jul. 24, 2014 for U.S. Appl. No. 13/630,674.
Office action dated Aug. 6, 2012 for U.S. Appl. No. 12/505,335.
Office action dated Sep. 4, 2013 for U.S. Appl. No. 13/630,674.
Office action dated Oct. 22, 2013 for U.S. Appl. No. 12/505,335.
Office action dated Oct. 27, 2011 for U.S. Appl. No. 12/505,335.
Office action dated Dec. 17, 2014 for U.S. Appl. No. 12/505,335.
Office action dated Dec. 17, 2014 for U.S. Appl. No. 13/630,674.
Sueda, et al. Efficacy of a simple left atrial procedure for chronic atrial fibrillation in mitral valve operations. Ann Thorac Surg. 1997; 63:1070-1075.
Sueda, et al. Simple left atrial procedure for chronic atrial fibrillation associated with mitral valve disease. Ann Thorac Surg 1996; 62:1796-1800.

(56) References Cited

OTHER PUBLICATIONS

Svilainis, et al. Power amplifier for ultrasonic transducer excitation. Ultragarsas, Ultrasound. 58.1. 2006: 30-36.
Ter Haar. Acoustic surgery. Physics Today. Dec. 2001; 54(12):29-34.
U.S. Appl. No. 13/360,674 Notice of Allowance dated Mar. 13, 2019.
U.S. Appl. No. 13/630,674, filed Sep. 28, 2012.
U.S. Appl. No. 13/630,674 Office Action dated Sep. 9, 2018.
U.S. Appl. No. 12/505,335 Notice of Allowance dated Feb. 27, 2019.
U.S. Appl. No. 12/505,335 Notice of Allowance dated Mar. 13, 2019.
U.S. Appl. No. 12/505,335 Office Action dated Oct. 4, 2018.

SYSTEM AND METHOD FOR DELIVERING ENERGY TO TISSUE

CROSS-REFERENCE TO RELATED APPLICATIONS

The present application is a continuation of U.S. patent application Ser. No. 13/630,674 filed Sep. 28, 2012, which is a continuation of U.S. patent application Ser. No. 12/505,335 filed Jul. 17, 2009, which is a non-provisional of, and claims the benefit of U.S. Provisional App. No. 61/082,064 filed Jul. 18, 2008, the entire contents of each are incorporated herein by reference.

BACKGROUND OF THE INVENTION

1. Field of the Invention

The present invention relates generally to medical devices, systems and methods, and more specifically to improved devices, systems and methods for creating an ablation zone in tissue. The device may be used to treat atrial fibrillation.

The condition of atrial fibrillation (AF) is characterized by the abnormal (usually very rapid) beating of the left atrium of the heart which is out of synch with the normal synchronous movement ("normal sinus rhythm") of the heart muscle. In normal sinus rhythm, the electrical impulses originate in the sino-atrial node ("SA node") which resides in the right atrium. The abnormal beating of the atrial heart muscle is known as fibrillation and is caused by electrical impulses originating instead in the pulmonary veins ("PV") [Haissaguerre, M. et al., Spontaneous Initiation of Atrial Fibrillation by Ectopic Beats Originating in the Pulmonary Veins, New England J Med., Vol. 339:659-666].

There are pharmacological treatments for this condition with varying degrees of success. In addition, there are surgical interventions aimed at removing the aberrant electrical pathways from the PV to the left atrium ("LA") such as the Cox-Maze III Procedure [J. L. Cox et al., The development of the Maze procedure for the treatment of atrial fibrillation, Seminars in Thoracic & Cardiovascular Surgery, 2000; 12: 2-14; J. L. Cox et al., Electrophysiologic basis, surgical development, and clinical results of the maze procedure for atrial flutter and atrial fibrillation, Advances in Cardiac Surgery, 1995; 6: 1-67; and J. L. Cox et al., Modification of the maze procedure for atrial flutter and atrial fibrillation. II, Surgical technique of the maze III procedure, Journal of Thoracic & Cardiovascular Surgery, 1995; 2110:485-95]. This procedure is shown to be 99% effective [J. L. Cox, N. Ad, T. Palazzo, et al. Current status of the Maze procedure for the treatment of atrial fibrillation, Seminars in Thoracic & Cardiovascular Surgery, 2000; 12: 15-19] but requires special surgical skills and is time consuming.

There has been considerable effort to copy the Cox-Maze procedure for a less invasive percutaneous catheter-based approach. Less invasive treatments have been developed which involve use of some form of energy to ablate (or kill) the tissue surrounding the aberrant focal point where the abnormal signals originate in the PV. The most common methodology is the use of radiofrequency ("RF") electrical energy to heat the muscle tissue and thereby ablate it. The aberrant electrical impulses are then prevented from traveling from the PV to the atrium (achieving conduction block within the heart tissue) and thus avoiding the fibrillation of the atrial muscle. Other energy sources, such as microwave, laser, and ultrasound have been utilized to achieve the conduction block. In addition, techniques such as cryoablation, administration of ethanol, and the like have also been used.

There has been considerable effort in developing catheter based systems for the treatment of AF using radiofrequency (RF) energy. One such method is described in U.S. Pat. No. 6,064,902 to Haissaguerre et al. In this approach, a catheter is made of distal and proximal electrodes at the tip. The catheter can be bent in a J shape and positioned inside a pulmonary vein. The tissue of the inner wall of the pulmonary vein (PV) is ablated in an attempt to kill the source of the aberrant heart activity. Other RF based catheters are described in U.S. Pat. No. 6,814,733 to Schwartz et al., U.S. Pat. No. 6,996,908 to Maguire et al., U.S. Pat. No. 6,955,173 to Lesh, and U.S. Pat. No. 6,949,097 to Stewart et al.

Another source used in ablation is microwave energy. One such device is described by Dr. Mark Levinson [(Endocardial Microwave Ablation: A New Surgical Approach for Atrial Fibrillation; The Heart Surgery Forum, 2006] and Maessen et al. [Beating heart surgical treatment of atrial fibrillation with microwave ablation. Ann Thorac Surg 74: 1160-8, 2002]. This intraoperative device consists of a probe with a malleable antenna which has the ability to ablate the atrial tissue. Other microwave based catheters are described in U.S. Pat. No. 4,641,649 to Walinsky; U.S. Pat. No. 5,246,438 to Langberg; U.S. Pat. No. 5,405,346 to Grundy et al.; and U.S. Pat. No. 5,314,466 to Stem et al.

Another catheter based method utilizes the cryogenic technique where the tissue of the atrium is frozen below a temperature of −60 degrees C. This results in killing of the tissue in the vicinity of the PV thereby eliminating the pathway for the aberrant signals causing the AF [A. M. Gillinov, E. H. Blackstone and P. M. McCarthy, Atrial fibrillation: current surgical options and their assessment, Annals of Thoracic Surgery 2002; 74:2210-7]. Cryo-based techniques have been a part of the partial Maze procedures [Sueda T., Nagata H., Orihashi K. et al., Efficacy of a simple left atrial procedure for chronic atrial fibrillation in mitral valve operations, Ann Thorac Surg 1997; 63:1070-1075; and Sueda T., Nagata H., Shikata H. et al.; Simple left atrial procedure for chronic atrial fibrillation associated with mitral valve disease, Ann Thorac Surg 1996; 62: 1796-1800]. More recently, Dr. Cox and his group [Nathan H., Eliakim M., The junction between the left atrium and the pulmonary veins, An anatomic study of human hearts, Circulation 1966; 34:412-422, and Cox J. L., Schuessler R. B., Boineau J. P., The development of the Maze procedure for the treatment of atrial fibrillation, Semin Thorac Cardiovasc Surg 2000; 12:2-14] have used cryoprobes (cryo-Maze) to duplicate the essentials of the Cox-Maze III procedure. Other cryo-based devices are described in U.S. Pat. Nos. 6,929,639 and 6,666,858 to Lafintaine and U.S. Pat. No. 6,161,543 to Cox et al.

More recent approaches for the AF treatment involve the use of ultrasound energy. The target tissue of the region surrounding the pulmonary vein is heated with ultrasound energy emitted by one or more ultrasound transducers. One such approach is described by Lesh et al. in U.S. Pat. No. 6,502,576. Here the catheter distal tip portion is equipped with a balloon which contains an ultrasound element. The balloon serves as an anchoring means to secure the tip of the catheter in the pulmonary vein. The balloon portion of the catheter is positioned in the selected pulmonary vein and the balloon is inflated with a fluid which is transparent to ultrasound energy. The transducer emits the ultrasound energy which travels to the target tissue in or near the pulmonary vein and ablates it. The intended therapy is to destroy the electrical conduction path around a pulmonary vein and thereby restore the normal sinus rhythm. The therapy involves the creation of a multiplicity of lesions around individual pulmonary veins as required. The inventors describe various configurations for the energy emitter and the anchoring mechanisms.

Yet another catheter device using ultrasound energy is described by Gentry et al. [Integrated Catheter for 3-D Intracardiac Echocardiography and Ultrasound Ablation, IEEE Transactions on Ultrasonics, Ferroelectrics, and Frequency Control, Vol. 51, No. 7, pp 799-807]. Here the catheter tip is made of an array of ultrasound elements in a grid pattern for the purpose of creating a three dimensional image of the target tissue. An ablating ultrasound transducer is provided which is in the shape of a ring which encircles the imaging grid. The ablating transducer emits a ring of ultrasound energy at 10 MHz frequency. In a separate publication [Medical Device Link, Medical Device and Diagnostic Industry, February 2006], in the description of the device, the authors assert that the pulmonary veins can be imaged.

While these devices and methods are promising, improved devices and methods for creating a heated zone of tissue, such as an ablation zone are needed. Furthermore, it would also be desirable if such devices could create single or multiple ablation zones to block abnormal electrical activity in the heart in order to lessen or prevent atrial fibrillation. It would also be desirable if such devices could be used in the presence of blood or other body tissues without coagulating or clogging up the ultrasound transducer. Such devices and methods should be easy to use, minimally invasive, cost effective and simple to manufacture.

2. Description of the Background Art

Other devices based on ultrasound energy to create circumferential lesions are described in U.S. Pat. Nos. 6,997, 925; 6,966,908; 6,964,660; 6,954,977; 6,953,460; 6,652, 515; 6,547,788; and 6,514,249 to Maguire et al.; U.S. Pat. Nos. 6,955,173; 6,052,576; 6,305,378; 6,164,283; and 6,012,457 to Lesh; U.S. Pat. Nos. 6,872,205; 6,416,511; 6,254,599; 6,245,064; and 6,024,740; to Lesh et al.; U.S. Pat. Nos. 6,383,151; 6,117,101; and WO 99/02096 to Diederich et al.; U.S. Pat. No. 6,635,054 to Fjield et al.; U.S. Pat. No. 6,780,183 to Jimenez et al.; U.S. Pat. No. 6,605,084 to Acker et al.; U.S. Pat. No. 5,295,484 to Marcus et al.; and WO 2005/117734 to Wong et al.

BRIEF SUMMARY OF THE INVENTION

The present invention relates generally to medical devices and methods, and more specifically to medical devices and methods used to deliver energy to tissue as a treatment for atrial fibrillation and other medical conditions.

In a first aspect of the present invention, an ablation system for treating atrial fibrillation in a patient comprises an elongate shaft having a proximal end, a distal end, and lumens therebetween. A housing is adjacent the distal end of the elongate shaft and an energy source is coupled to the housing. The energy source is adapted to deliver energy to a target tissue so as to create a zone of ablation in the target tissue that blocks abnormal electrical activity thereby reducing or eliminating the atrial fibrillation in the patient. The system also has a reflecting element operably coupled with the energy source and adapted to redirect energy emitted from the energy source in a desired direction or pattern.

The housing may be rotatable about its longitudinal axis and the energy may be redirected by the reflecting element in a generally circular pattern. The energy source may be recessed from a distal end of the housing such that the energy source does not contact the target tissue in operation.

The energy source may comprise an ultrasound transducer that is adapted to emit a beam of ultrasound energy. The beam may have a frequency in the range of 5 to 20 MHz and a generator may be electrically coupled with the ultrasound transducer. The generator may provide an excitation voltage of 5 to 300 volts peak-to-peak to the ultrasound transducer. The excitation voltage may have a duty cycle ranging from 0% to 100%, and may have a repetition frequency of about 40 KHz. The energy source may be adapted to deliver one of radiofrequency energy, microwaves, photonic energy, thermal energy, and cryogenic energy. The energy source may comprise a flat face, a concave face or a convex face. The face may be adapted to act as a lens for focusing the energy delivered by the energy source.

The system may comprise a sensor adjacent the energy source and that is adapted to detect relative position of the energy source to the target tissue or characteristics of the target tissue. The sensor may be adapted to detect a gap between a surface of the target tissue and the energy source. The sensor may be adapted to determine characteristics of the target tissue such as tissue thickness or ablation zone depth. The sensor may comprise an ultrasound transducer. The energy source may comprise the same ultrasound transducer as the sensor. Other sensors may comprise an infrared sensor or strain gage.

The reflecting element may be non-expandable. It may redirect the energy in a collimated beam through a portion of the housing or it may redirect the energy in a focused beam that converges toward a focal point or a focal ring, or it may alter the focus of the beam to provide a more uniformly collimated beam. The reflecting element may comprise an angled outer surface that is adapted to redirect the energy. The angle of the outer surface may range from 30 to 60 degrees relative to a longitudinal axis of the housing. The angled face may comprise a flat surface. The reflecting element may comprise a curved outer surface that redirects the energy. The reflecting element may redirect the energy through a sidewall of the housing. The reflecting element may be movable relative to the energy source so that the energy exits the housing at varying angles or so that the energy is reflected outward away from the housing in a circular pattern. The reflecting element may be adapted to redirect the energy from the energy source to form a ring shaped beam of energy. The reflecting element may comprise a liquid-gas interface or a bowl-shaped reflector that is centered around a longitudinal axis of the housing. The liquid-gas interface may comprise a plurality of expandable reflectors positioned adjacent one another. The reflecting element may comprise two reflecting portions each having a different shape or angle relative to the energy source so that the energy is redirected in two or more directions or patterns. The energy may be redirected in a first pattern comprising a collimated beam and the energy may be redirected in a second pattern comprising a focused beam.

The system may further comprise a processor that is adapted to control the energy provided by the energy source based on information received from the sensor. The system may have a lens adjacent the energy source and that is adapted to adjust beam pattern of the energy emitted from the energy source.

The target tissue may comprise left atrial tissue, a pulmonary vein or tissue adjacent thereto. The zone of ablation may comprise a linear ablation path or an arcuate ablation path. The zone of ablation may comprise a transmural ablation zone.

In another aspect of the present invention, a method for treating atrial fibrillation by ablating tissue in a patient comprises providing an ablation system comprising an elongate shaft having a distal tip assembly. The distal tip assembly comprises an energy source and a reflecting element. The distal tip assembly is advanced adjacent the tissue and energy is delivered from the energy source to the tissue. Energy from the energy source is reflected off of the reflecting element so as to redirect the energy emitted from the energy source in a desired direction or pattern. A partial or complete zone of ablation is created in the tissue, thereby blocking abnormal electrical activity and reducing or eliminating the atrial fibrillation.

The step of advancing the distal tip assembly may comprise passing the distal tip through an atrial septal wall. The energy source may comprise an ultrasound transducer and the step of delivering the energy may comprise delivering a beam of ultrasound. The beam may comprise a frequency in the range of 5 to 20 MHz. Delivering the energy may comprise providing an excitation voltage ranging from 5 to 300 volts peak-to-peak to the ultrasound transducer. Delivering energy may comprise delivering one of radiofrequency energy, microwaves, photonic energy, thermal energy and cryogenic energy.

The step of reflecting the energy may comprise redirecting the energy in a collimated beam of energy or focusing the energy so that it converges toward a focal point or a focal ring. Reflecting the energy may comprise redirecting the energy so that it exits a sidewall of the housing. The reflecting element may be non-expandable or it may comprise an expandable member such as a balloon or collapsible nested reflectors (e.g. similar to a collapsible parabolic dish used in satellite communications), and the step of reflecting the energy may comprise expanding the expandable member. Reflecting the energy may comprise moving the reflecting element relative to the housing such as by rotating it. The reflecting element may comprise a first reflecting portion and a second reflecting portion. The energy reflected off the first portion may be redirected in a first direction, and the energy reflected off the second portion may be redirected in a second direction different than the first direction.

The zone of ablation may comprise a linear or arcuate zone of ablation. The step of creating the zone of ablation may comprise encircling the zone of ablation around a pulmonary vein or left atrial tissue. The zone of ablation may comprise a transmural lesion.

The method may further comprise cooling the energy source with a cooling fluid. The system may further comprise a sensor that is adapted to sense relative position of the energy source to the target tissue or characteristics of the target tissue. The ablation system may further comprise a processor, and the method may further comprise controlling energy delivery based on information from the sensor.

The method may comprise sensing a gap distance between the energy source and a surface of the tissue with the sensor. The method may also include sensing characteristics of the tissue such as tissue thickness or depth of the ablation zone, with the sensor. The sensor may comprise an ultrasound sensor and the energy source may also comprise the same ultrasound transducer. The method may include switching modes between delivering energy with the ultrasound transducer and sensing tissue characteristics with the ultrasound transducer sensor.

These and other embodiments are described in further detail in the following description related to the appended drawing figures.

DETAILED DESCRIPTION OF THE INVENTION

The following description of preferred embodiments of the invention is not intended to limit the invention to these embodiments, but rather to enable any person skilled in the art to make and use this invention.

Figure 1:
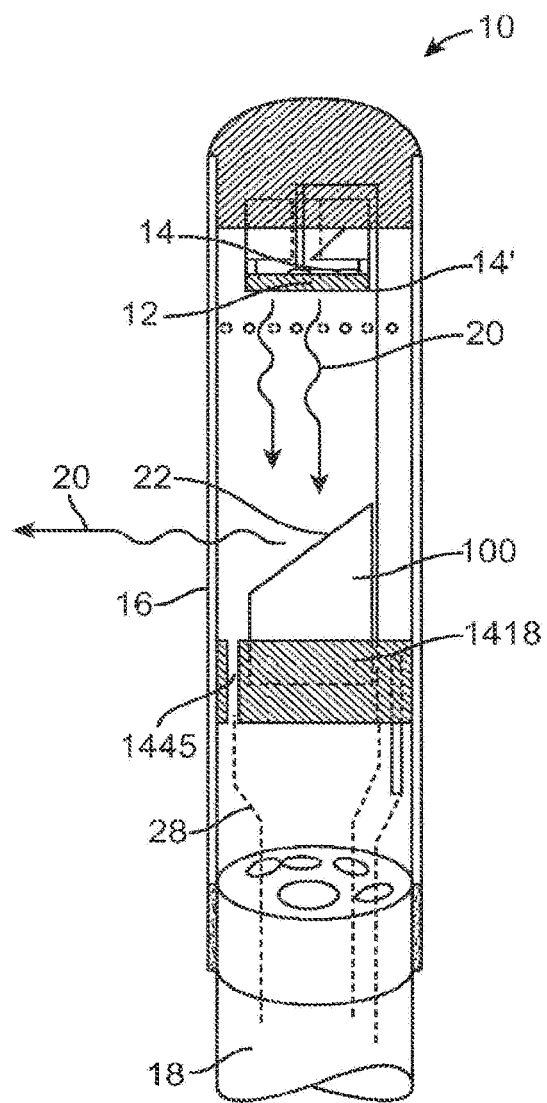
FIGS. 1 and 2 are drawings of the system of the preferred embodiments of the invention.

As shown in FIG. 1, the energy delivery system 10 of the preferred embodiments includes an energy source 12 that functions to provide a source of ablation energy; a reflecting surface 100 that functions to redirect the ablation energy from the energy source 12; a sensor; and a processor (not shown), coupled to the sensor and to the energy source 12, which may controls the energy source 12 based on the information from the sensor. The energy delivery system 10 is preferably designed for delivering energy to tissue, more specifically, for delivering ablation energy to tissue, such as heart tissue, to create a conduction block—isolation and/or block of conduction pathways of abnormal electrical activity, which typically originate from the pulmonary veins in the left atrium—for treatment of atrial fibrillation in a patient. The system 10, however, may be alternatively used with any suitable tissue in any suitable environment and for any suitable reason.

The Energy Source. As shown in FIG. 1, the energy source 12 of the preferred embodiments functions to provide a source of ablation energy. The ablation energy is preferably in the form of an energy beam 20 emitted from the energy source 12. The energy source 12 is preferably an ultrasound transducer that emits an ultrasound beam, but may alternatively be any suitable energy source that functions to provide a source of ablation energy. Some suitable sources of ablation energy may include radio frequency (RF) energy, microwaves, photonic energy, and thermal energy. The therapy could alternatively be achieved using cooled fluids (e.g., cryogenic fluid). The energy delivery system 10 preferably includes a single energy source 12, but may alternatively include any suitable number of energy sources 12. For example, the system 10 may include multiple energy sources configured in a ring, such that in combination they emit an annular shaped energy beam 20.

Figure 2:
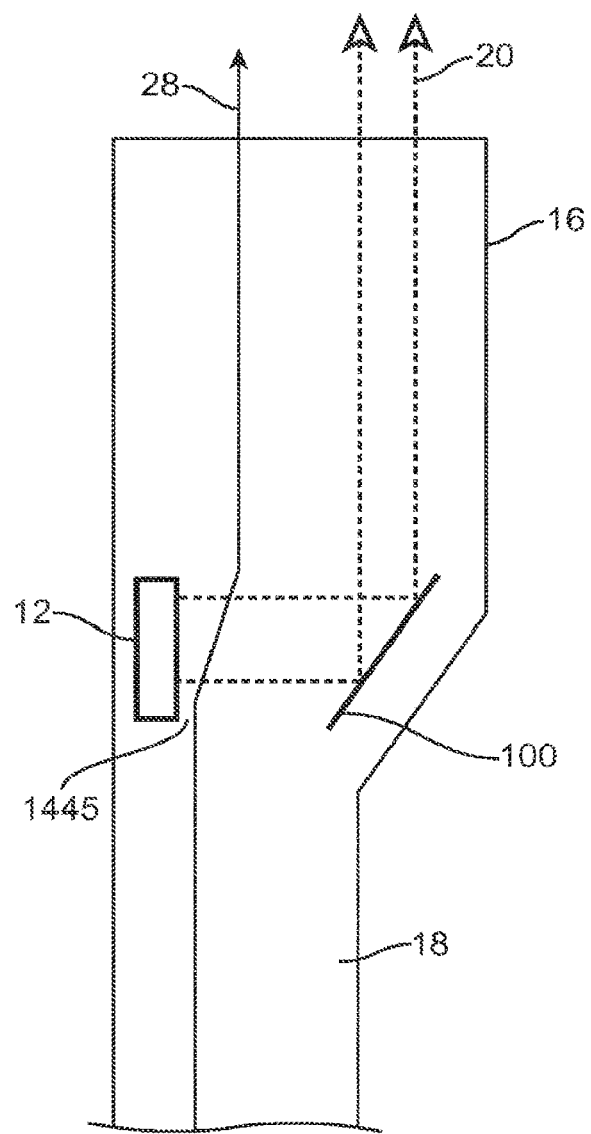
Figure 3A:
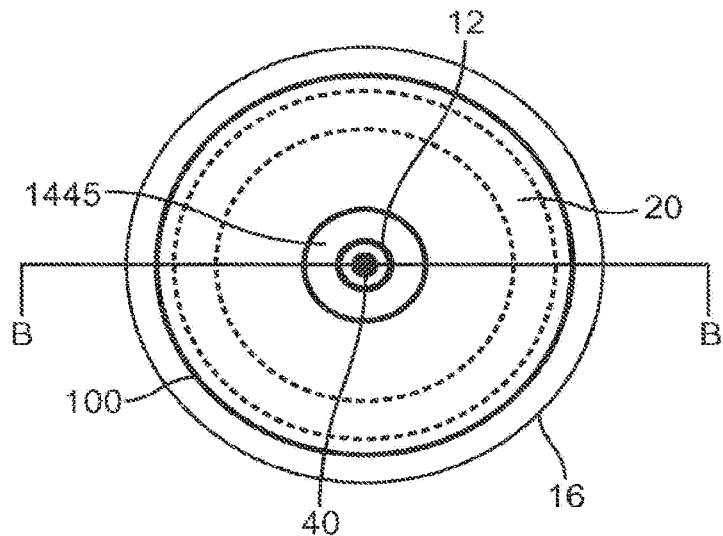
FIGS. 3A-3B illustrate the reflecting surface of the system and energy beam of the preferred embodiments of the invention.
Figure 3B:
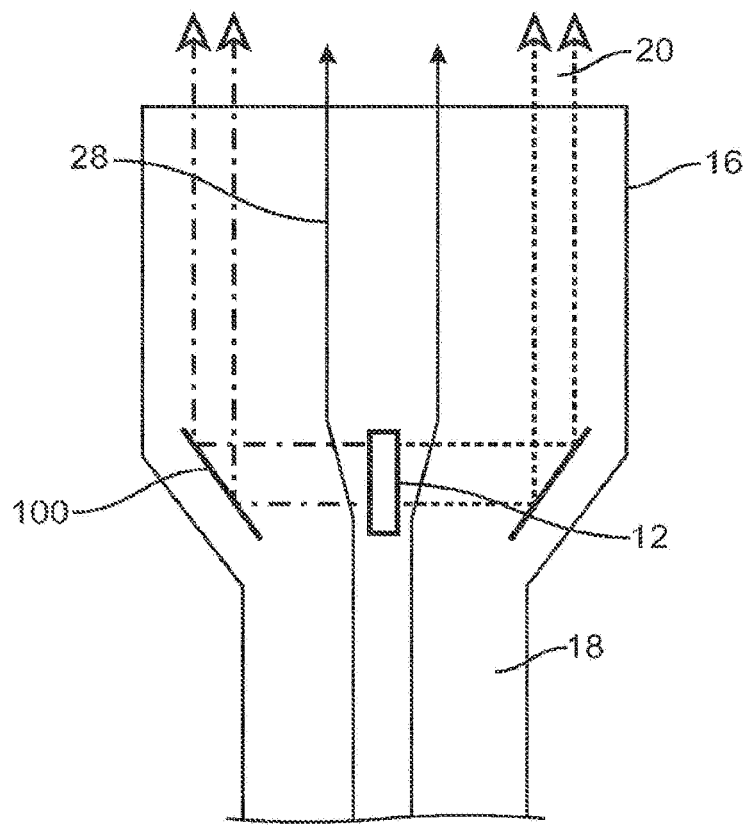

The energy source 12 is preferably an ultrasound transducer that is preferably made of a piezoelectric material such as PZT (lead zirconate titanate) or PVDF (polyvinylidine difluoride), or any other suitable ultrasound beam emitting material. The transducer may further include coating layers such as a thin layer of a metal. Some suitable transducer coating metals may include gold, stainless steel, nickel-cadmium, silver, plastic, metal-filled graphite, a metal alloy, and any other suitable material that functions to increase the efficiency of coupling of the energy beam 20 into the surrounding fluid 28 or performs any other suitable functions. The transducer is preferably a cylindrical transducer, as shown in FIGS. 3A and 3B, such that it preferably emits energy beam 20 from the outer face of the cylinder (e.g. radially out from the face of the energy source). The energy beam 20 is preferably emitted radially 360 degrees around the energy source 12, but may alternatively be emitted from any suitable portions) of the energy source. The transducer may alternatively be a generally flat transducer, such as a disc, as shown in FIGS. 1 and 2. The disc transducer preferably emits energy beam 20 from at least one of the faces of the disc. The faces of the disc that emit the energy beam 20 are preferably flat, but may alternatively be either concave or convex to achieve an effect of a lens. The disc transducer preferably has a circular geometry, but may alternatively be elliptical, polygonal, doughnut shaped, or any other suitable shape.

As shown in FIG. 1, the energy source 12 of the preferred embodiments is preferably coupled to at least one electrical attachment 14. The electrical attachment 14 of the preferred embodiments functions to energize the energy source 12 such that it emits an energy beam 20. The energy delivery system 10 preferably includes two electrical attachments 14 and 14', but may alternatively include any suitable number of electrical attachments to energize the energy source 12. The energy delivery system 10 of the preferred embodiments also includes an electrical generator (not shown) that functions to provide power to the energy source 12 via the electrical attachment(s) 14. When energized by the generator the energy source 12 emits an energy beam 20. The generator provides the appropriate frequency and voltage to the energy source 12 to create the desired energy beam 20. In the case of an ultrasound energy source 12, the ultrasound frequency is preferably in the range of 1 to 25 MHz and more preferably in the range of 5 to 20 MHz. The energy of the energy beam 20 is determined by the excitation voltage applied to the energy source 12. The voltage is preferably in the range of 5 to 300 volts peak-to-peak. In addition, a variable duty cycle is preferably used to control the average power delivered to the energy source 12. The duty cycle preferably ranges from 0% to 100%, with a repetition frequency of approximately 40 kHz, which is preferably faster than the time constant of thermal conduction in the tissue.

Figure 4:
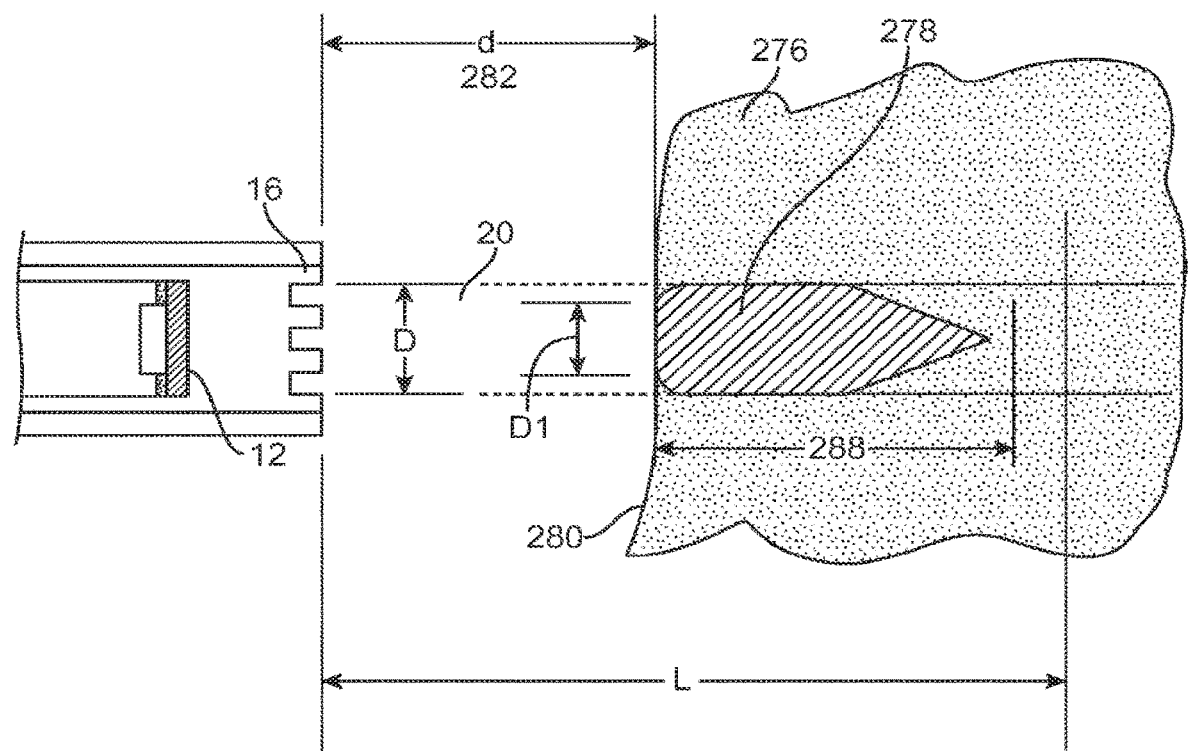
FIG. 4-5 are drawings of the energy beam and the zone of ablation of the preferred embodiment of the invention.

When energized with an electrical pulse or pulse train by the electrical attachment 14 and/or 14', the energy source 12 emits an energy beam 20 (such as a sound wave). The properties of the energy beam 20 are determined by the characteristics of the energy source 12, the matching layer, the backing (described below), and the electrical pulse from electrical attachment 14. These elements determine the frequency, bandwidth, and amplitude of the energy beam 20 (such as a sound wave) propagated into the tissue. As shown in FIG. 4, the energy source 12 emits energy beam 20 such that it interacts with tissue 276 and forms a lesion (zone of ablation 278). The energy beam 20 is preferably an ultrasound beam. The tissue 276 is preferably presented to the energy beam 20 within the collimated length L. The front surface 280 of the tissue 276 is at a distance d (282) away from the face of a housing 16. As the energy beam 20 travels through the tissue 276, its energy is absorbed by the tissue 276 and converted to thermal energy. This thermal energy heats the tissue to temperatures higher than the surrounding tissue resulting in a heated zone 278. In the zone 278 where the tissue is heated, the tissue cells are preferably rendered dead due to heat. The temperatures of the tissue are preferably above the temperature where cell death occurs in the heated zone 278 and therefore, the tissue is said to be ablated. Hence, the zone 278 is preferably referenced as the ablation zone or lesion.

The shape of the lesion or ablation zone 278 formed by the energy beam 20 depends on the characteristics of suitable combination factors such as the energy beam 20, the energy source 12 (including the material, the geometry, the portions of the energy source 12 that are energized and/or not energized, etc.), the matching layer, the backing, the electrical pulse from electrical attachment 14 (including the frequency, the voltage, the duty cycle, the length of the pulse, etc.), and the characteristics of target tissue that the beam 20 contacts and the length of contact or dwell time. These characteristics can be changed based on the information detected by the sensor (as described below), thereby changing the physical characteristics of the lesion.

The housing 16 also functions to provide a barrier between the face of the energy source 12 and blood or tissue. When fluid flow is incorporated, the fluid may flow past the energy source thereby preventing blood from coagulating thereon. In preferred embodiments, the coolant flows past the energy source at approximately 1 ml/minute, but may be increased or decreased as desired. Additionally, since the energy source is disposed in the housing, the energy source will not directly contact tissue, thereby also preventing coagulation on the energy source.

Additional details on the energy source, energy source configurations, the housing and adjacent components are disclosed in US20090312693A1, U.S. patent application Ser. No. 12/480,256 and US20090312673A1, U.S. patent application Ser. No. 12/482,640, the entire contents of which are incorporated herein by reference.

Figure 7:
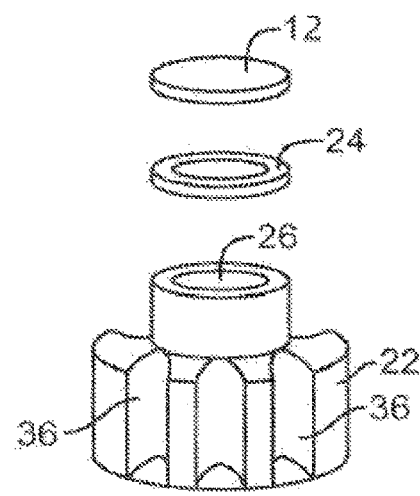
FIG. 7 illustrates the energy source having a backing.
Figure 8A:
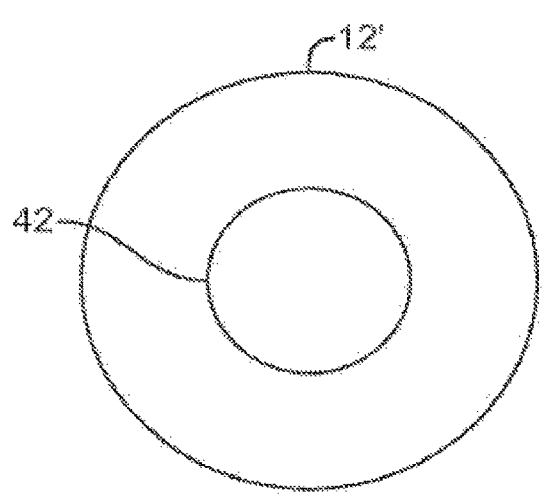
FIGS. 8A-8B illustrate other embodiments of the energy source.
Figure 8B:
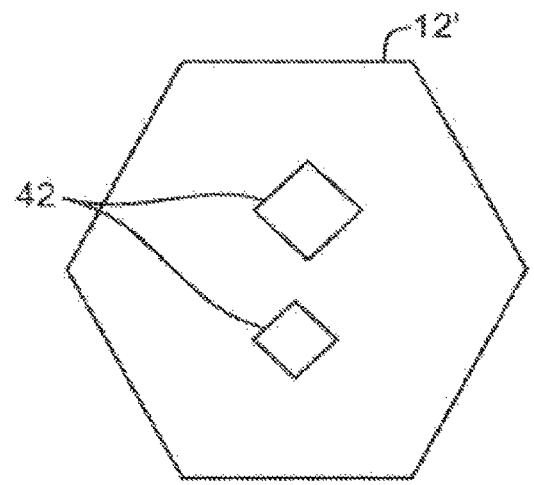

The energy source 12 is preferably one of several variations. In a first variation, as shown in FIG. 7, the energy source 12 is a disc with a flat front surface. In a second variation, as shown in FIGS. 8A and 8B, the energy source 12' includes an inactive portion 42. In this variation, the inactive portion 42 does not emit an energy beam when the energy source 12 is energized, or may alternatively emit an energy beam with a very low (substantially zero) energy. The inactive portion 42 preferably functions to aid in the temperature regulation of the energy source, i. e. preventing the energy source from becoming too hot. In a full disk transducer, as shown in FIG. 7, the center portion of the transducer generally becomes the hottest portion of the transducer while energized. By removing the center portion or a portion of the center portion of the transducer, the energy emitted from the transducer is preferably distributed differently across the transducer, and the heat of the transducer is preferably more easily dissipated.

The inactive portion 42 is preferably a hole or gap defined by the energy source 12'. In this variation, a coolant source may be coupled to, or in the case of a coolant fluid, it may flow through the hole or gap defined by the energy source 12' to further cool and regulate the temperature of the energy source 12'. The inactive portion 42 may alternatively be made of a material with different material properties from that of the energy source 12'. For example, the material is preferably a metal, such as copper, which functions to draw or conduct heat away from the energy source 12. Alternatively, the inactive portion is made from the same material as the energy source 12, but with the electrode plating removed or disconnected from the electrical attachments 14 and or the generator. The inactive portion 42 is preferably disposed along the full thickness of the energy source 12', but may alternatively be a layer of material on or within the energy source 12' that has a thickness less than the full thickness of the energy source 12'. As shown in FIG. 8A, the energy source 12' is preferably a doughnut-shaped transducer. As shown, the transducer preferably defines a hole (or inactive portion 42) in the center portion of the transducer. The energy source 12' of this variation preferably has a circular geometry, but may alternatively be elliptical, polygonal (FIG. 8B), or any other suitable shape. The energy source 12' preferably includes a singular, circular inactive portion 42, but may alternatively include any suitable number of inactive portions 42 of any suitable geometry, as shown in FIG. 8B. The total energy emitted from the energy source 12 is related to the surface area of the energy source 12 that is active (ke. emits energy beam 20). Therefore, the size and location of inactive portions 42 preferably reduce heat build-up in the energy source 12, while allowing the energy source 12 to provide as much output energy as possible or as desired.

Figure 6:
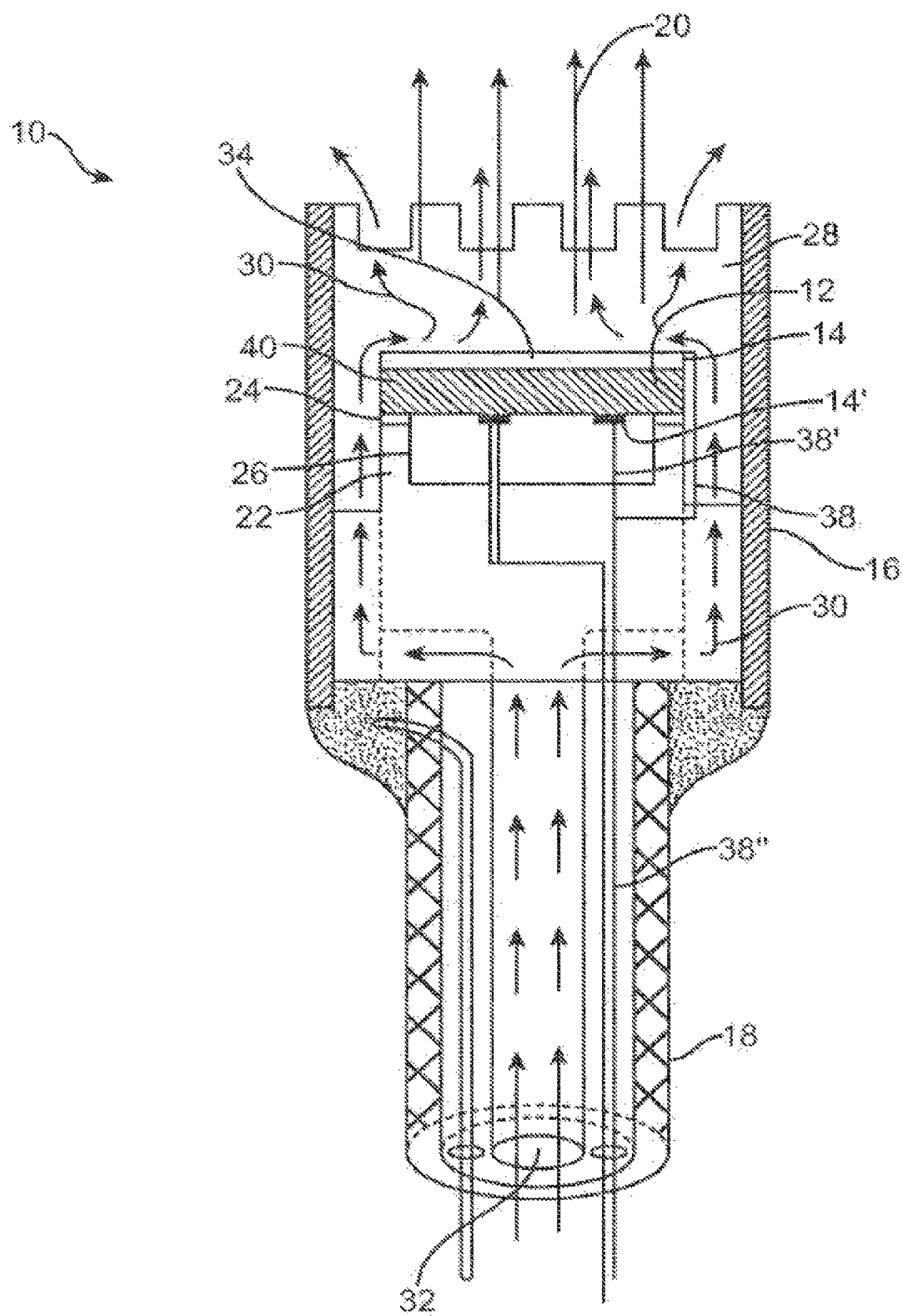
FIG. 6 illustrates an embodiment of the system.

As shown in FIGS. 6 and 7, the energy delivery system 10 of the preferred embodiments also includes a backing 22, coupled to the energy source 12. The energy source 12 is preferably bonded to the end of a backing 22 by means of an adhesive ring 24. Backing 22 is preferably made of a metal or a plastic, such that it provides a heat sink for the energy source 12. The attachment of the energy source 12 to the backing 22 is such that there is a pocket 26 between the back surface of the energy source 12 and the backing 22. This pocket preferably contains a material with acoustic impedance significantly different than the material of the energy source 12, and preferably creates an acoustically reflective surface. Most of the ultrasound that would otherwise exit from the back of the energy source 12 is preferably redirected back into the energy source 12 from the pocket, and out through the front surface of the energy source 12. Additionally, the material in the pocket is also preferably a good thermal conductor, so that heat can be removed from the energy source, and electrically conductive such that it may connect the electrical wires to the rear surface of the energy source. The pocket is preferably one of several variations. In a first version, the backing 22 couples to the energy source at multiple points. For example, the backing preferably includes three posts that preferably couple to the outer portion such that the majority of the energy source 12 is not touching a portion of the backing. In this variation, a fluid or gel preferably flows past the energy source 12, bathing preferably both the front and back surfaces of the energy source 12. In a second variation, the pocket is an air pocket 26 between the back surface of the energy source 12 and the backing 22. The air pocket 26 functions such that when the energy source 12 is energized by the application of electrical energy, the emitted energy beam 20 is reflected by the air pocket 26 and directed outwards from the energy source 12. The backing 22 preferably defines an air pocket of a cylindrical shape, and more preferably defines an air pocket 26 that has an annular shape. The backing defines an annular air pocket by further including a center post such that the backing is substantially tripod shaped when viewed in cross section, wherein the backing is coupled to the energy source 12 towards both the outer portion of the energy source and towards the center portion of the energy source. The air pocket 26 may alternatively be replaced by any other suitable material such that a substantial portion of the energy beam 20 is directed outwards from the energy source 12.

While the energy source 12 is emitting an energy beam 20, the energy source may become heated. The energy source 12 is preferably maintained within a safe operating temperature range by cooling the energy source 12. Cooling of the energy source 12 is preferably accomplished by contacting the energy source 12 with a fluid, for example, saline or any other physiologically compatible fluid, preferably having a lower temperature relative to the temperature of the energy source 12. In a first version, the temperature of the fluid is preferably cold enough that it both cools the transducer and the target tissue. In this version, the temperature of the fluid or gel is preferably between −5 and 5 degrees Celsius and more preferably substantially equal to zero degrees Celsius. In a second version, the temperature of the fluid is within a temperature range such that the fluid cools the energy source 12, but it does not cool the target tissue however, and may actually warm the target tissue. The fluid may alternatively be any suitable temperature to sufficiently cool the energy source 12. By way of an example, as shown in FIG. 7, the backing 22 preferably has a series of grooves 36 disposed longitudinally along the outside wall that function to provide for the flow of a cooling fluid 2S substantially along the outer surface of backing 22 and past the face of the energy source 12. The series of grooves may alternatively be disposed along the backing in any other suitable configuration, such as helical. The resulting fluid flow lines are depicted as 30 in FIG. 6. The flow of the cooling fluid is achieved through a lumen 32. The fluid used for cooling the transducer preferably exits the housing 16 through the end of the housing 16 or through one or more apertures. The apertures are preferably a grating, screen, holes, drip holes, weeping structure or any of a number of suitable apertures. The fluid preferably exits the housing 16 to contact the target tissue and to cool the tissue.

The Reflecting Surface. As shown in FIG. 1, the reflector 100 of the preferred embodiments functions to redirect the energy beam 20 from the energy source 12. The reflecting surface 100 preferably redirects the energy beam 20 from the energy source 12 out of housing 16 and preferably towards the target tissue. The reflecting surface 100 preferably redirects the energy beam 20 such that it is a collimated beam exiting the housing 16 (as shown in FIGS. 2 and 3), the reflecting surface 22 may alternatively redirect the energy beam 20 such that it is a focused beam that preferably converges towards a substantially single focal point or towards focal point ring. The reflecting surface is preferably one of several variations. In a first variation, as shown in FIG. 1, the reflecting surface 100 is an angled reflector device. The reflector device is preferably a cylindrical reflector with a face of the reflector at an angle to the longitudinal axis of the housing 16. The energy source 12 is preferably positioned towards the distal end of the housing 16 with the front face pointing towards the reflector device, which is preferably positioned along the same axis (the longitudinal axis of the housing 16) as the energy source 12. The energy beam 20 from the energy source 12 is preferably redirected from the reflecting surface such that it exits the housing 16 through a side portion of the housing. The reflector device is preferably made from a material that reflects the energy beam 20, such as metal, but may alternatively be a gas filled reflector device such as a gas filled balloon. The angled face of the reflector is preferably flat, but may alternatively be a non-planar face, such as a curved, convex or concave surface. The angle of the reflector preferably ranges between substantially 0 degrees, more preferably substantially 30-60 degrees, and most preferably substantially 45 degrees. The reflector device is preferably set at a fixed angle with respect to the energy source 12, but may alternatively be movable, such as rotated or pivoted, to alter the angle that the energy beam 20 will exit the housing 16. Referring to FIG. 1, the reflector device is preferably secured to the housing 16 by means of a distal adhesive band 1418, but may alternatively be coupled to the housing 16 with any other suitable chemical and/or mechanical connection such as adhesive, welding, pins and/or screws. The adhesive band 1418 preferably includes a passageway 1445 for the flow of a cooling fluid (as described below).

In the first variation of the reflecting surface 100, the energy beam 20 exiting from the housing 16 is preferably directed along an ablation path such that it propagates into tissue. As the energy beam 20 propagates into the tissue along the ablation path, it preferably provides a partial or complete zone of ablation along the ablation path. The zone of ablation along the ablation path preferably has any suitable geometry to provide therapy, such as providing a conduction block for treatment of atrial fibrillation in a patient. The zone of ablation along the ablation path may alternatively provide any other suitable therapy for a patient. A linear ablation path is preferably created by moving the system 10, and the energy source 12 within it, in an X, Y, and/or Z direction. A generally circular or elliptical ablation path is preferably created by rotating the energy source 12 about an axis. In a first version, the reflecting surface 100 is preferably rotated within the housing 16 and about the longitudinal axis of the housing 16, such that as the energy source 12 is energized and emitting the energy beam 20, the beam will be reflected out of the housing in 360 degrees. The energy beam 20 that is redirected by the reflecting surface 100 preferably exits a side portion of the housing though a window located around the circumference of the distal tip assembly 16. The window is preferably made of a material that is transparent to ultrasound waves such as a poly 4-methyl, 1-pentene (PMP) material or may alternatively be an open window. In a second version, the entire system 10 will rotate, rotating the energy beam 20 that exits from at least one single portion of the housing 16. The system 10 is preferably rotated about the longitudinal axis of the housing 16, but may alternatively be rotated about an axis off set from the longitudinal axis of the housing 16. In this version, the energy beam 20 preferably sweeps a generally circular path.

In a second variation, as shown in FIG. 2, the reflecting surface 100 is also an angled reflector device. The reflector device is preferably a substantially flat reflecting device, with an inside face of the reflector at an angle to the front face of the energy source 12. The energy source 12 is preferably positioned adjacent to a side wall of the housing 16 with the front face the energy source 12 pointing towards the reflector device. The energy beam 20 from the energy source 12 is preferably redirected from the reflecting surface such that it exits the housing 16 through an end portion of the housing. The energy beam 20 that is redirected by the reflecting surface 100 preferably exits the end portion of the housing though a window. The window is preferably an open window, but may alternatively be made of a material that is transparent to ultrasound waves such as a poly 4-methyl, 1-pentene (PMP) material. The reflector device is preferably made from a material that reflects the energy beam 20, such as metal, but may alternatively be a gas filled reflector device such as a gas filled balloon. The angled face of the reflector is preferably flat, but may alternatively be a nonplanar face, such as a curved, convex or concave surface. The angle of the reflector preferably ranges between substantially 0-90 degrees, more preferably substantially 30-60 degrees, and most preferably substantially 45 degrees. The reflector device is preferably set at a fixed angle with respect to the energy source 12, but may alternatively be movable, such as rotated or pivoted, to alter the angle that the energy beam 20 will exit the housing 16. The reflecting surface 22 preferably includes a passageway 1445 for the flow 28 of a cooling fluid (as described below).

In the second variation of the reflecting surface 100, the energy beam 20 exiting from the housing 16 is preferably directed along an ablation path such that it propagates into tissue. As the energy beam 20 propagates into the tissue along the ablation path, it preferably provides a partial or complete zone of ablation along the ablation path. A linear ablation path is preferably created by moving the system 10, and the energy source 12 within it, in an X, Y, and/or Z direction. Alternatively, a generally circular or elliptical ablation path is preferably created by rotating the housing 16 about an axis. In a first version, the housing 16 is preferably rotated about its longitudinal axis. Because the energy beam 20 is redirected by the reflecting surface 100, as shown in FIG. 2, the energy beam 20 exits the housing at a distance from the longitudinal axis of the housing. Therefore, as the housing 16 is moved in a circular or elliptical path, the energy beam 20 will contact the tissue, creating a corresponding generally circular or elliptical ablation path.

In a third variation, as shown in FIGS. 3A and 3B, the reflecting surface 100 is also an angled, bowl-shaped reflector device centered around the longitudinal axis of the housing 16. The inside surface of the reflector device is preferably a substantially linear surface (in cross section, as shown in FIG. 3B) at an angle to the front face of the energy source 12. The angled face of the reflector is preferably flat, but may alternatively be a non-planar face, such as a curved, convex or concave surface, or combinations thereof. The energy source 12 is preferably a cylindrical energy source 12, positioned along the longitudinal axis of the housing 16. The energy beam 20 from the energy source 12 preferably exits the energy source radially and is preferably redirected from the reflecting surface such that it exits the housing 16 as a ring shaped energy beam (as shown in FIG. 3A) through an end portion of the housing. The energy beam 20 that is redirected by the reflecting surface 100 preferably exits the end portion of the housing though a window. The window is preferably an open window, but may alternatively be made of a material that is transparent to ultrasound waves such as a poly 4-methyl, 1-pentene (PMP) material. The reflector device is preferably made from a material that reflects the energy beam 20, such as metal, but may alternatively be a gas filled reflector device such as a gas filled balloon. The angle of the reflector preferably ranges between substantially 0-90 degrees, more preferably substantially 30-60 degrees, and most preferably substantially 45 degrees. The reflector device is preferably set at a fixed angle with respect to the energy source 12, but may alternatively be movable, such as rotated or pivoted, to alter the angle that the energy beam 20 will exit the housing 16.

In the third variation of the reflector 100, the energy beam 20 exiting from the housing 16 is preferably ring-shaped, as shown in FIG. 3A, and therefore preferably creates a ring shaped ablation path when it interacts with tissue and preferably provides a partial or complete zone of ablation along the ablation path. A linear ablation path is alternatively created by the energy source 12 emitting energy beam 20 from only a partial radial portion of the energy source and/or by moving the system 10, and the energy source 12 within it, in an X, Y, and/or Z direction. Alternatively, the energy source of the third variation reflecting surface 100 may be a flat energy source (rather than a cylindrical one) with the front face towards a portion of the reflecting surface. To create an ablation path, the energy source 12 is preferably rotated about the longitudinal axis of the housing such that the energy beam 20 will be redirected by various portions of the reflecting surface, creating a circular ablation path.

Figure 5:
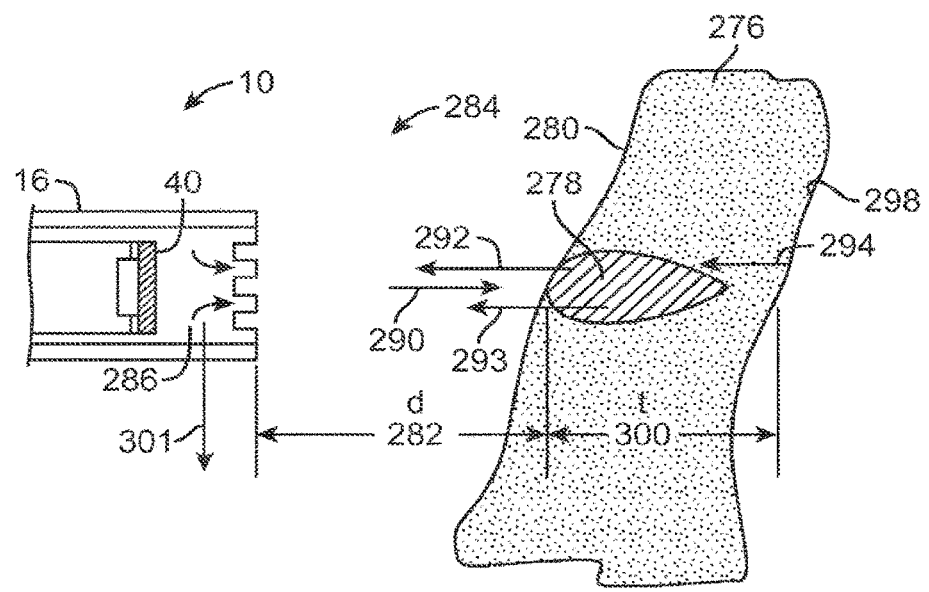

The Sensor. As shown in FIG. 5, the energy delivery system 10 of the preferred embodiments also includes a sensor that functions to detect the gap (e.g., the distance of the tissue surface from the energy source 12), the thickness of the tissue targeted for ablation, and the characteristics of the ablated tissue. The sensor is preferably an ultrasound transducer, but may alternatively be any suitable sensor, such as a strain gage, feeler gage, or IR sensor, to detect information with respect to the gap, the thickness of the tissue targeted for ablation, the characteristics of the ablated tissue, the location of elements of the system 10, and/or any other suitable parameter or characteristic.

The sensor is preferably the same transducer as the transducer of the energy source 12 operating in a different mode (such as A-mode, defined below), but may alternatively be a separate ultrasound transducer or an additional sensor 40' as shown in FIG. 3A coupled to a top portion of the cylindrical energy source 12. The system 10 may include multiple sensors such as a first sensor to detect information with respect to the target tissue, and a second sensor to detect information with respect to the location of the elements of the system 10. By detecting information on the gap, the thickness of the tissue targeted for ablation, the characteristics of the ablated tissue, and/or the locations of the elements of the system 10, the sensor preferably functions to guide the therapy provided by the ablation of the tissue.

In the variations of the system 10 wherein the sensor is the same transducer as the transducer of the energy source 12 operating in a different mode (such as A-mode), the sensor preferably utilizes a pulse of ultrasound of short duration, which is generally not sufficient for heating of the tissue. This is a simple ultrasound imaging technique, referred to in the art as A Mode, or Amplitude Mode imaging. As shown in FIG. 5, sensor 40 preferably sends a pulse 290 of ultrasound towards the tissue 276. A portion of the beam is reflected and backscattered as 292 from the front surface 280 of the tissue 276. This reflected beam 292 is detected by the sensor 40 a short time later and converted to an electrical signal, which is sent to the electrical receiver (not shown). The reflected beam 292 is delayed by the amount of time it takes for the sound to travel from the sensor 40 to the front boundary 280 of the tissue 276 and back to the sensor 40. This travel time represents a delay in receiving the electrical signal from the sensor 40. Based on the speed of sound in the intervening media (fluid 286 and blood 284), the gap distance d (282) is determined. As the sound beam travels further into the tissue 276, a portion 293 of it is scattered from the lesion 278 being formed and travels towards the sensor 40. Again, the sensor 40 converts this sound energy into electrical signals and a processor (described below) converts this information into characteristics of the lesion formation such as thickness, etc. As the sound beam travels still further into the tissue 276, a portion 294 of it is reflected from the back surface 298 and travels towards the transducer. Again, the sensor 40 converts this sound energy into electrical signals and the processor converts this information into the thickness t (300) of the tissue 276 at the point of the incidence of the ultrasound pulse 290. As the catheter housing 16 is traversed in a manner 301 across the tissue 276, the sensor 40 detects the gap distance d (282), lesion characteristics, and the tissue thickness t (300). The sensor preferably detects these parameters continuously, but may alternatively detect them periodically or in any other suitable fashion. This information is used in delivering continuous ablation of the tissue 276 during therapy as discussed below.

The Processor. The energy delivery system 10 of the preferred embodiments also includes a processor, coupled to the sensor 40 and to the electrical attachment 14, that controls the electrical pulse delivered to the electrical attachment 14 and may modify the electrical pulse delivered based on the information from the sensor 40. The processor is preferably a conventional processor or logic machine that can execute computer programs including a microprocessor or integrated circuit, but may alternatively be any suitable device to perform the desired functions.

The processor preferably receives information from the sensor such as information related to the gap distance, the thickness of the tissue targeted for ablation, the characteristics of the ablated tissue, and any other suitable parameter or characteristic. Based on this information, the processor converts this information into a gap distance, a thickness of the tissue targeted for ablation, a characteristic of the ablated tissue, and any other suitable parameter or characteristic and/or controls the energy beam 20 emitted from the energy source 12 by modifying the electrical pulse sent to the energy source 12 via the electrical attachment 14 such as the frequency, the voltage, the duty cycle, the length of the pulse, and/or any other suitable parameter. The processor preferably also controls the energy beam 20 by controlling which portions of the energy source 12 are energized and/or at which frequency, voltage, duty cycle, etc. different portions of the energy source 12 are energized. Additionally, the processor may further be coupled to a fluid flow controller. The processor preferably controls the fluid flow controller to increase or decrease fluid flow based on the sensor detecting characteristics of the ablated tissue, of the unablated or target tissue, and/or any other suitable condition.

By controlling the energy beam 20 (and/or the cooling of the targeted tissue), the shape of the ablation zone 278 is controlled. For example, the depth 288 of the ablation zone is preferably controlled such that a transmural (through the thickness of the tissue) lesion is achieved. Additionally, the processor preferably functions to minimize the possibility of creating a lesion beyond the targeted tissue, for example, beyond the outer atrial wall. If the sensor detects the lesion extending beyond the outer wall of the atrium or that the depth of the lesion has reached or exceeded a preset depth, the processor preferably turns off the generator and/or ceases to send electrical pulses to the electrical attachment(s) 14. Additionally, if the sensor detects, for example, that the system 10 is not centered with respect to the pulmonary vein PV by detecting the distance of the target tissue with respect to the energy source and/or intended ablation path, the processor may either turn off the generator and/or cease to send electrical pulses to the electrical attachment(s) 14, may alter the pulses sent to the electrical attachment, and/or may alter the operator or motor drive unit to reposition the system with respect to the target tissue.

Additional Elements. As shown in FIG. 1, the energy delivery system 10 of the preferred embodiments may also include an elongate member 18, coupled to the energy source 12. The elongate member 18 is preferably a catheter made of a flexible multi-lumen tube, but may alternatively be a cannula, tube or any other suitable elongate structure having one or more lumens. The elongate member 18 of the preferred embodiments functions to accommodate pull wires, fluids, gases, energy delivery structures, electrical connections, therapy catheters, navigation catheters, pacing catheters, and/or any other suitable device or element. As shown in FIG. 1, the elongate member 18 preferably includes a housing 16 positioned at a distal portion of the elongate member 18 that functions to enclose the energy source 12 and the reflection surface 100. The elongate member 18 further functions to move and position the energy source 12 and/or the housing 16 within a patient, such that the emitted energy beam 20 contacts the target tissue at an appropriate angle and the energy source 12 and/or the housing 16 is moved along an ablation path such that the energy source 12 provides a partial or complete zone of ablation along the ablation path.

The energy delivery system 10 of the preferred embodiments may also include a lens or mirror, operably coupled to the energy source 12, that functions to provide additional flexibility in adjusting the beam pattern of the energy beam 20. The lens is preferably a standard acoustic lens, but may alternatively be any suitable lens to adjust the energy beam 20 in any suitable fashion. The lens may be used to focus or defocus the energy beam. For example, an acoustic lens could create a beam that is more uniformly collimated, such that the minimum beam width $D.sub.1$ approaches the diameter D of the energy source 12. This will provide a more uniform energy density in the ablation window, and therefore more uniform lesions as the tissue depth varies within the window. A lens could also be used to move the position of the minimum beam width $D.sub.1$, for those applications that may need either shallower or deeper lesion. This lens could be fabricated from plastic or other material with the appropriate acoustic properties, and bonded to the face of energy source 12. Alternatively, the energy source 12 itself may have a geometry such that it functions as a lens, or the matching layer or coating of the energy source 12 may function as a lens.

Although omitted for conciseness, the preferred embodiments include every combination and permutation of the various energy sources 12, electrical attachments 14, energy beams 20, sensors 40, and processors.

As a person skilled in the art will recognize from the previous detailed description and from the figures and claim, modifications and changes can be made to the preferred embodiments of the invention without departing from the scope of this invention defined in the following claims.

What is claimed is:

1. A system for ablating tissue, said system comprising:
an elongate shaft having a movable distal portion; and
an ablation element comprising an ultrasound transducer coupled to the movable distal portion of the elongate shaft;
wherein:
the ultrasound transducer comprises a single ultrasound transducer element having an active portion and an inactive portion;
the ultrasound transducer is configured to sense a thickness of a target tissue; and
the ultrasound transducer is configured to deliver a collimated beam of ultrasound energy comprising ablation energy to ablate the target tissue without contacting the target tissue with the elongate shaft or any structure disposed thereon.

2. The system of claim 1, further comprising a reflecting element operably coupled with the ultrasound transducer, the reflecting element redirecting the beam of ultrasound energy emitted from the ultrasound transducer to change a direction or a pattern of the beam of ultrasound energy.

3. The system of claim 2, wherein the reflecting element is non-expandable.

4. The system of claim 2, wherein the reflecting element is configured to move relative to the ultrasound transducer so that the beam of ultrasound energy is emitted at varying angles or positions.

5. The system of claim 1, wherein the system is configured to direct the beam of ultrasound energy along a path such that a zone of ablation in the target tissue has a ring shape, elliptical shape, linear shape, curvilinear shape, or combinations thereof.

6. The system of claim 1, further comprising a processor configured to adjust the beam of ultrasound energy in response to the sensed thickness of the target tissue.

7. The system of claim 6, wherein the processor is configured to adjust one or more of frequency, a voltage, a duty cycle, a pulse length, or a position of the beam of ultrasound energy in response to the sensed thickness of the target tissue.

8. The system of claim 1, further comprising a backing layer coupled to the ultrasound transducer, the backing layer configured to provide a heat sink for the ultrasound transducer.

9. The system of claim 8, wherein the backing layer comprises a plurality of grooves extending longitudinally along an outside wall of the backing layer.

10. The system of claim 1, wherein the inactive portion comprises a material configured to conduct heat away from the active portion.

11. The system of claim 1, further comprising a flow of fluid configured to cool the ultrasound transducer.

12. A method for ablating tissue, said method comprising:
providing an ablation system comprising an elongate shaft and an ablation element comprising an ultrasound transducer, wherein the ultrasound transducer comprises a single ultrasound transducer element having an active portion and an inactive portion;
positioning the ablation element adjacent a target tissue;
delivering a collimated beam of ultrasound energy comprising ablation energy from the ultrasound transducer to the target tissue without contacting the target tissue with the elongate shaft or any structure disposed thereon;
sensing a thickness of the target tissue with the ultrasound transducer; and
ablating at least a portion of the target tissue with the beam of ultrasound energy, thereby forming a zone of ablation comprising a continuous lesion in the target tissue.

13. The method of claim 12, wherein delivering the collimated beam of ultrasound energy comprises reflecting the beam of ultrasound energy off of a reflecting element operably coupled with the ultrasound transducer thereby redirecting the beam of ultrasound energy and changing a direction or pattern of the beam of ultrasound energy.

14. The method of claim 13, wherein reflecting the beam of ultrasound energy comprises moving the reflecting element relative to the ultrasound transducer so that the beam of ultrasound energy is emitted at varying angles or positions.

15. The method of claim 12, further comprising directing the beam of ultrasound energy along a path such that the zone of ablation in the target tissue has a ring shape, elliptical shape, linear shape, curvilinear shape, or combinations thereof.

16. The method of claim 12, further comprising adjusting the beam of ultrasound energy in response to the sensed thickness of the target tissue.

17. The method of claim 16, wherein adjusting the beam of ultrasound energy comprises adjusting one or more of frequency, a voltage, a duty cycle, a pulse length, or a position of the beam of ultrasound energy in response to the sensed thickness of the target tissue.

18. The method of claim 12, further comprising cooling the ultrasound transducer.

19. The method of claim 18, wherein the inactive portion comprises a material configured to conduct heat away from the active portion.

20. The method of claim 18, wherein the ablation system further comprises a backing layer coupled to the ultrasound transducer, the backing layer configured to provide a heat sink for the ultrasound transducer, wherein the backing layer comprises a plurality of grooves extending longitudinally along an outside wall of the backing layer.

* * * * *